United States Patent [19]

Posakony et al.

[11] 4,170,142
[45] Oct. 9, 1979

[54] LINEAR TRANSDUCER ARRAY AND METHOD FOR BOTH PULSE-ECHO AND HOLOGRAPHIC ACOUSTIC IMAGING

[75] Inventors: Gerald J. Posakony; B. Percy Hildebrand; Thomas J. Davis, all of Richland, Wash.

[73] Assignee: Electric Power Research Institute, Inc., Palo Alto, Calif.

[21] Appl. No.: 816,095

[22] Filed: Jul. 15, 1977

[51] Int. Cl.² .............................................. G01N 29/04
[52] U.S. Cl. ...................................... 73/603; 73/617; 73/626; 73/641
[58] Field of Search ................. 73/617, 618, 619, 625, 73/626, 628, 641, 642, 603, 605, 633; 340/1 R, 3 R, 9

[56] References Cited

U.S. PATENT DOCUMENTS

| | | | |
|---|---|---|---|
| 3,135,944 | 6/1964 | Ehrlich | 340/9 |
| 3,166,731 | 1/1965 | Joy | 340/15 |
| 3,400,363 | 9/1968 | Silverman | 340/3 |
| 3,416,366 | 12/1968 | Beaujard et al. | 73/642 |
| 3,461,420 | 8/1969 | Silverman | 340/1 |
| 3,548,644 | 12/1970 | O'Connor et al. | 73/71.5 |
| 3,620,070 | 11/1971 | Collins | 73/629 |
| 3,685,051 | 8/1972 | Wells | 73/67.5 H X |
| 3,693,415 | 9/1972 | Whittington | 73/67.9 |
| 3,717,843 | 2/1973 | Farrah et al. | 340/1 R |
| 3,778,756 | 12/1973 | Houston | 340/3 R X |
| 3,778,757 | 12/1973 | Houston | 340/3 R X |
| 3,789,350 | 1/1974 | Rolle | 340/3 R |
| 3,789,833 | 2/1974 | Bom | 73/67.7 X |
| 3,803,606 | 4/1974 | Lebail | 343/17 |
| 3,820,387 | 6/1974 | Grabendorfer et al. | 73/626 |
| 3,852,745 | 12/1974 | Lebail | 343/17 |
| 3,911,730 | 10/1975 | Niklas | 73/626 X |
| 3,919,683 | 11/1975 | Itamura et al. | 340/1 R |
| 3,936,791 | 2/1976 | Kossoff | 340/1 R |

Primary Examiner—James J. Gill
Attorney, Agent, or Firm—Flehr, Hohbach, Test, Albritton & Herbert

[57] ABSTRACT

A linear transducer array for transmitting and receiving acoustic waves in both pulse-echo and holographic modes of operation. For pulse-echo acoustic imaging the array includes a linear subarray of transmitting transducer elements disposed in a plane along a longitudinal axis. Each transmitting element has an elongate shape and a principal axis that is perpendicular to the longitudinal axis of the array. For holographic imaging the apparatus further includes a removable mechanical shutter for blocking a predetermined portion of the principal axis of each of the transmitting elements so that a dispersive acoustic beam can be generated. The array also includes a linear subarray of receiving transducer elements coplanar with the transmitting subarray and disposed parallel to the longitudinal axis. The subarray of receiving elements is used to detect the reflected acoustic waves for both holographic and pulse-echo imaging.

20 Claims, 14 Drawing Figures

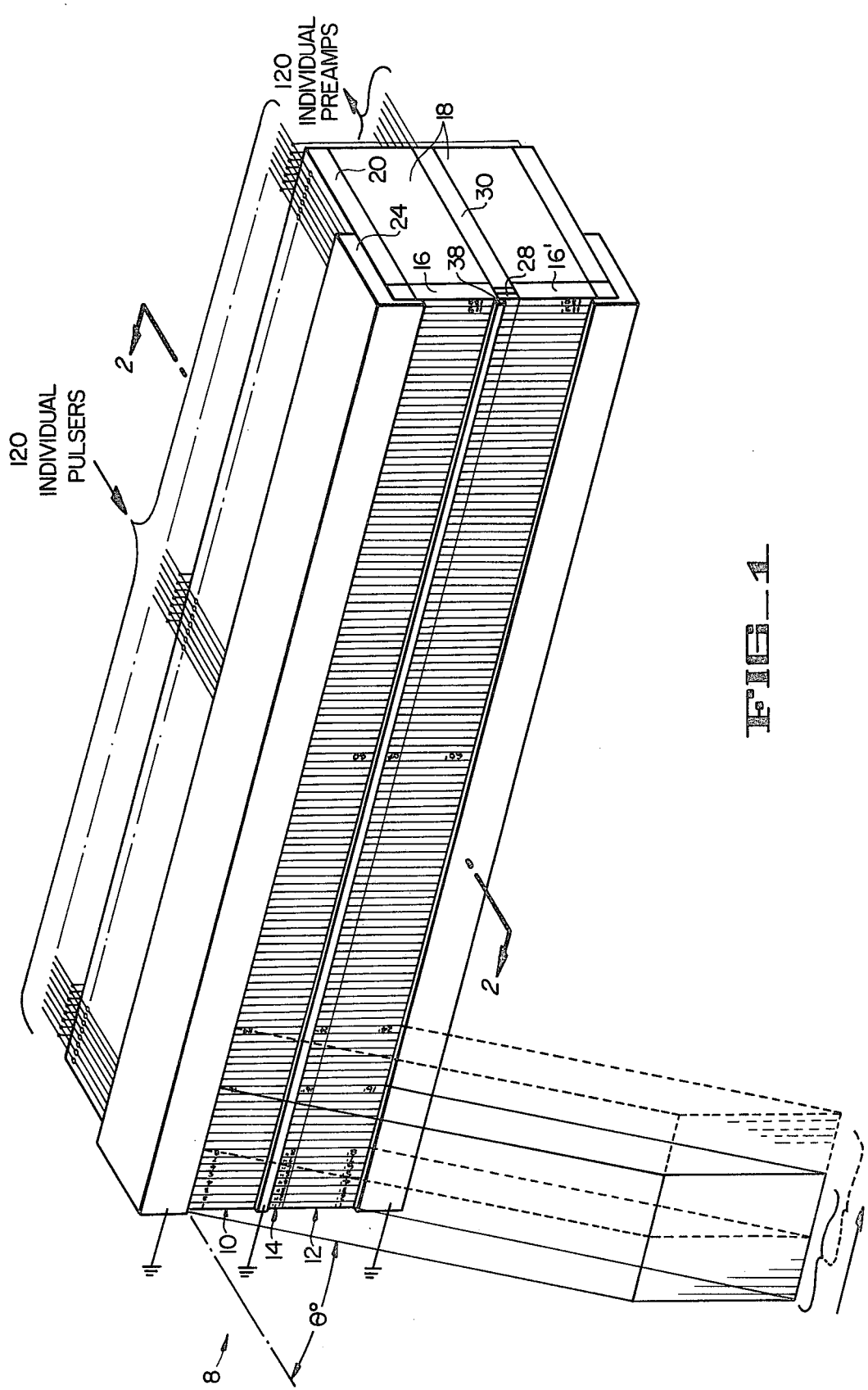
FIG_1

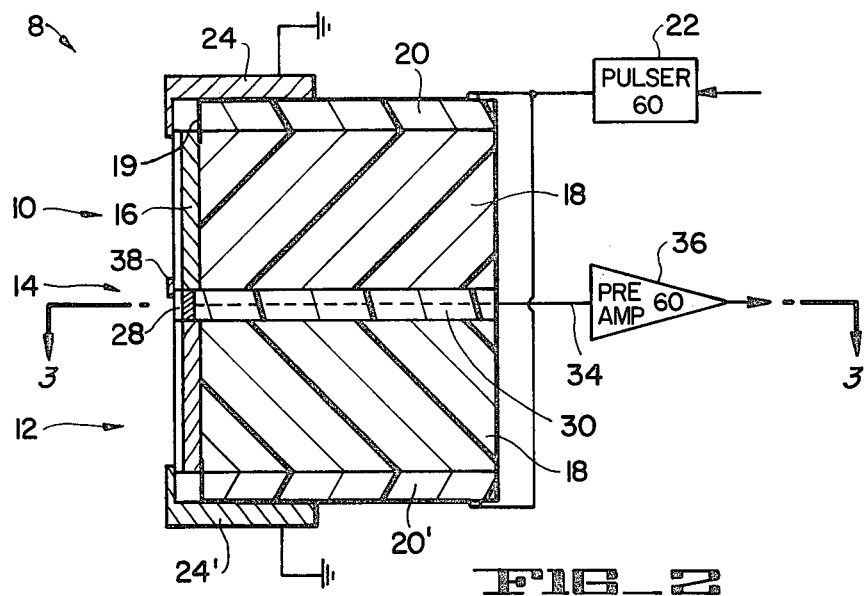
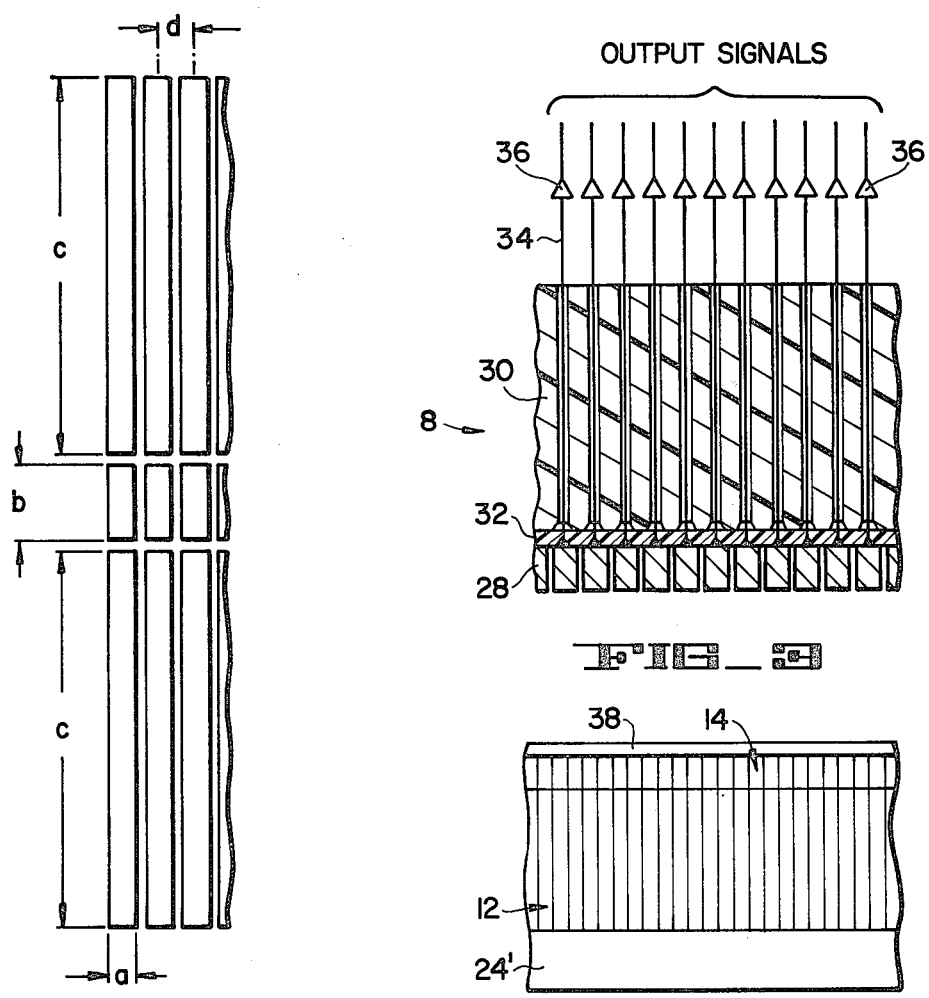

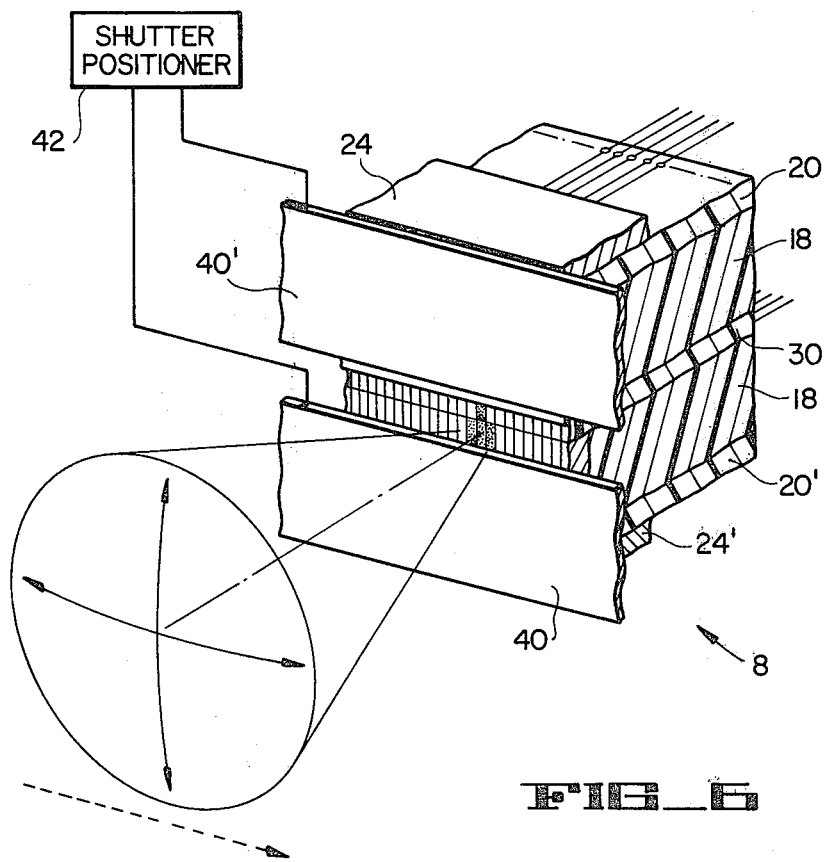
FIG_6
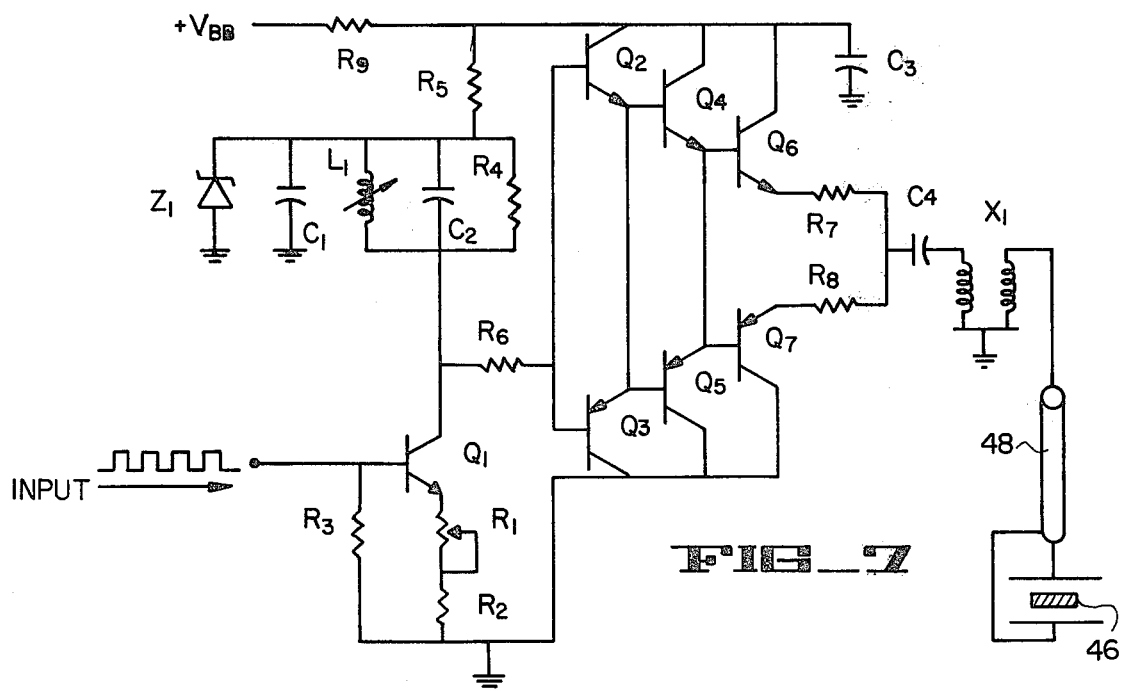
FIG_7

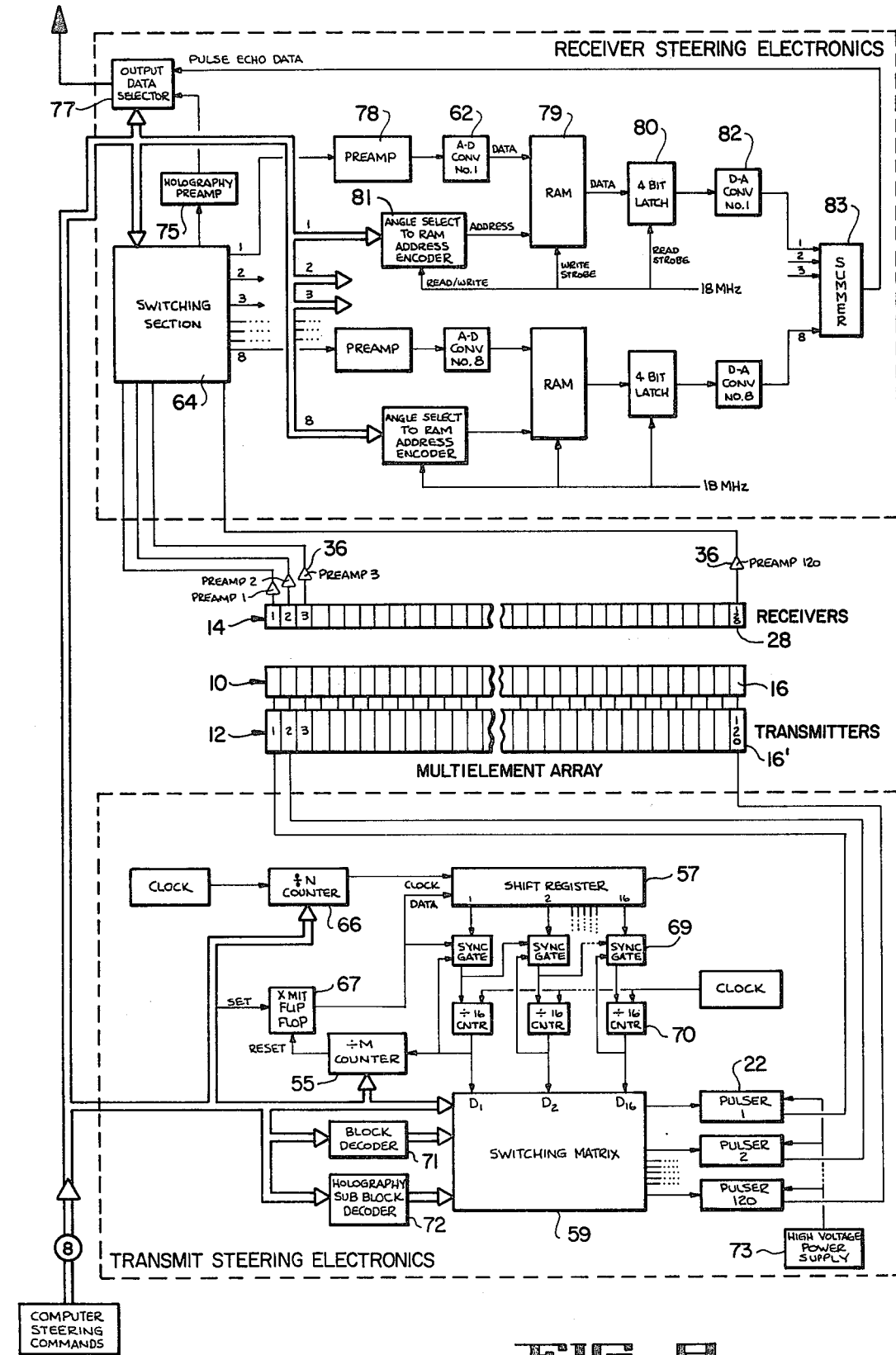
FIG_8

| BLOCK SELECTED → | 1 | 2 | 3 | 4 | 5 | 6 | 7 | 8 | 9 | 10 | 11 | 12 | 13 | 14 | | HOLOGRAPHIC SUB-BLOCKS | | |
|---|---|---|---|---|---|---|---|---|---|---|---|---|---|---|---|---|---|---|
| DELAY TIME WHEN ENERGIZED | | | | | | | | | | | | | | | | | | |
| −ANGLES | +ANGLES | | | | | | | | | | | | | | | | | |
| 16 | 1 | 1 | 9 | 17 | 25 | 33 | 41 | 49 | 57 | 65 | 73 | 81 | 89 | 97 | 105 | 1 | | |
| 15 | 2 | 2 | 10 | 18 | 26 | 34 | 42 | 50 | 58 | 66 | 74 | 82 | 90 | 98 | 106 | | 2 | |
| 14 | 3 | 3 | 11 | 19 | 27 | 35 | 43 | 51 | 59 | 67 | 75 | 83 | 91 | 99 | 107 | | | 3 |
| 13 | 4 | 4 | 12 | 20 | 28 | 36 | 44 | 52 | 60 | 68 | 76 | 84 | 92 | 100 | 108 | 4 | | |
| 12 | 5 | 5 | 13 | 21 | 29 | 37 | 45 | 53 | 61 | 69 | 77 | 85 | 93 | 101 | 109 | | 5 | |
| 11 | 6 | 6 | 14 | 22 | 30 | 38 | 46 | 54 | 62 | 70 | 78 | 86 | 94 | 102 | 110 | | | 6 |
| 10 | 7 | 7 | 15 | 23 | 31 | 39 | 47 | 55 | 63 | 71 | 79 | 87 | 95 | 103 | 111 | 7 | | |
| 9 | 8 | 8 | 16 | 24 | 32 | 40 | 48 | 56 | 64 | 72 | 80 | 88 | 96 | 104 | 112 | | 8 | |
| 8 | 9 | 9 | 17 | 25 | 33 | 41 | 49 | 57 | 65 | 73 | 81 | 89 | 97 | 105 | 113 | | | 9 |
| 7 | 10 | 10 | 18 | 26 | 34 | 42 | 50 | 58 | 66 | 74 | 82 | 90 | 98 | 106 | 114 | 10 | | |
| 6 | 11 | 11 | 19 | 27 | 35 | 43 | 51 | 59 | 67 | 75 | 83 | 91 | 99 | 107 | 115 | | 11 | |
| 5 | 12 | 12 | 20 | 28 | 36 | 44 | 52 | 60 | 68 | 76 | 84 | 92 | 100 | 108 | 116 | | | 12 |
| 4 | 13 | 13 | 21 | 29 | 37 | 45 | 53 | 61 | 69 | 77 | 85 | 93 | 101 | 109 | 117 | 13 | | |
| 3 | 14 | 14 | 22 | 30 | 38 | 46 | 54 | 62 | 70 | 78 | 86 | 94 | 102 | 110 | 118 | | 14 | |
| 2 | 15 | 15 | 23 | 31 | 39 | 47 | 55 | 63 | 71 | 79 | 87 | 95 | 103 | 111 | 119 | | | |
| 1 | 16 | 16 | 24 | 32 | 40 | 48 | 56 | 64 | 72 | 80 | 88 | 96 | 104 | 112 | 120 | | | |
TRANSMITTER ELEMENT NUMBERS
TRANSMITTER ELEMENT SELECTION
FIG_9
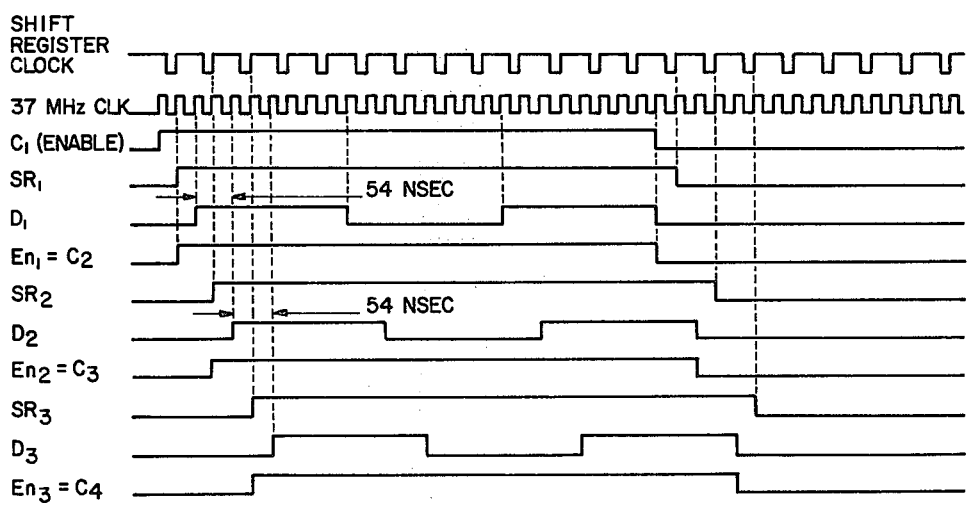
TRANSMITTER TIMING DIAGRAM
FIG_10

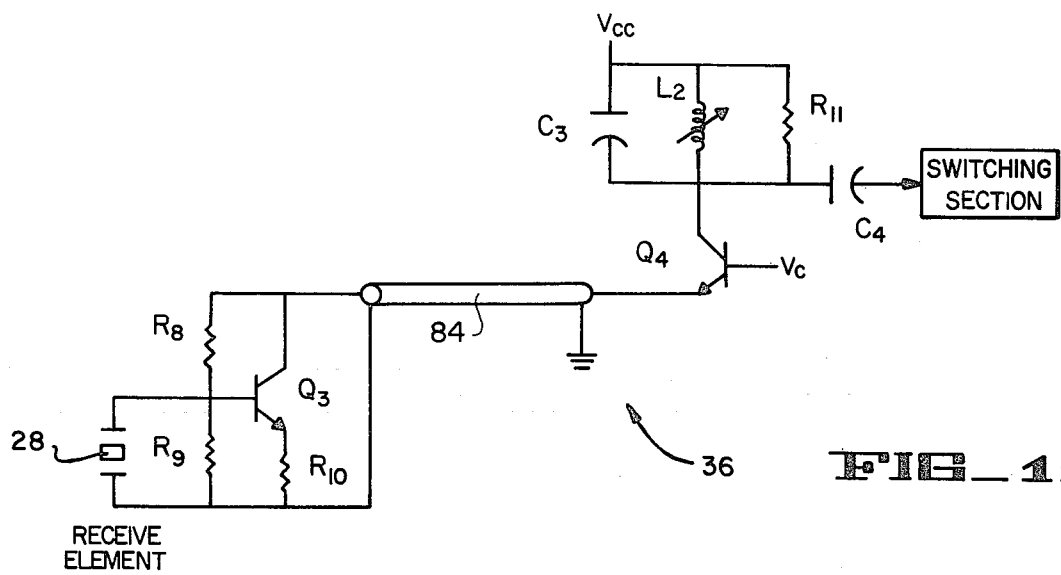
FIG_11
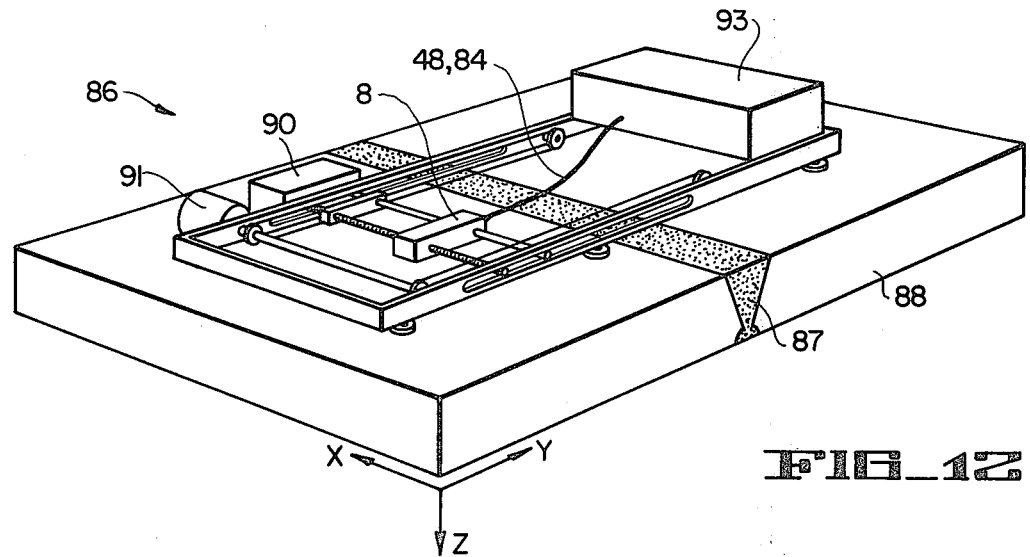
FIG_12
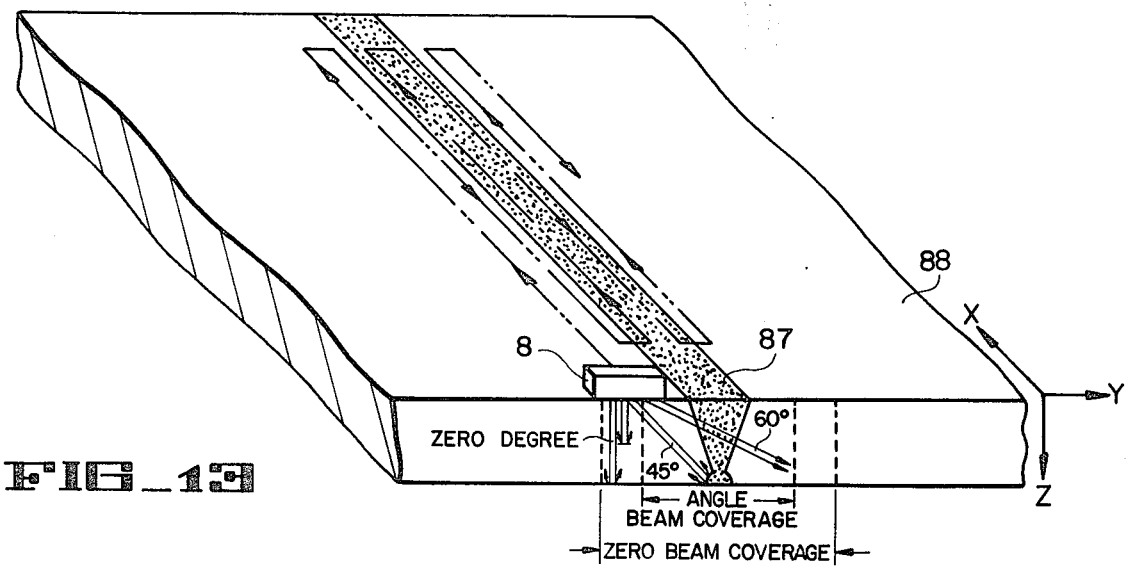
FIG_13

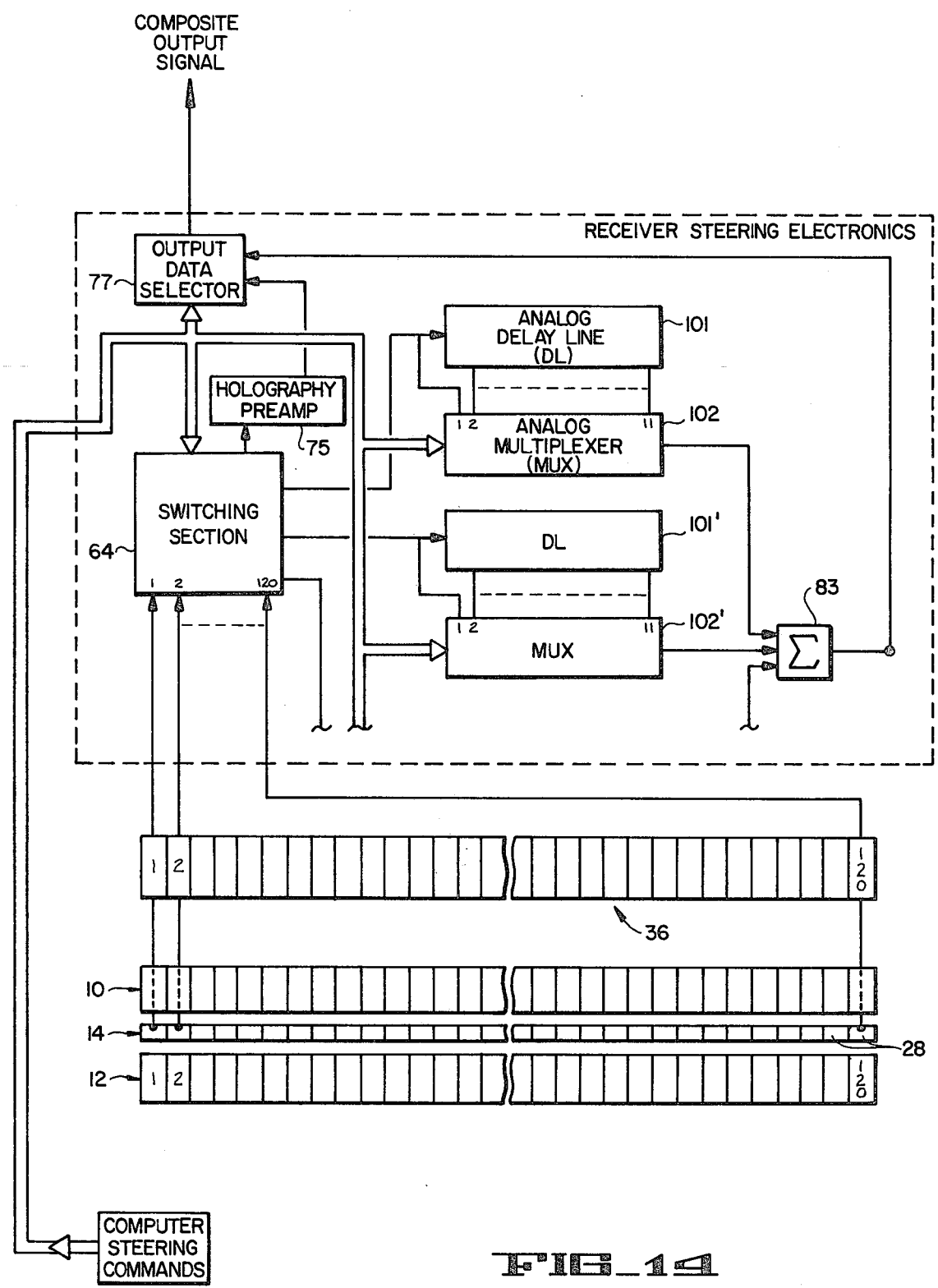

LINEAR TRANSDUCER ARRAY AND METHOD FOR BOTH PULSE-ECHO AND HOLOGRAPHIC ACOUSTIC IMAGING

BACKGROUND OF THE INVENTION

1. Field of the Invention

The present invention generally relates to acoustic transducers and, in particular, to linear transducer arrays that can perform either or both pulse-echo and holographic acoustic imaging.

2. Description of the Prior Art

The American Society of Mechanical Engineers (ASME) Boiler and Pressure Vessel Code Section XI, 1974 Edition, "Rules For the Inspection of Nuclear Power Plant Components" and the Summer 1974 Addenda sets down the requirements for volumetric inservice inspection of welds in nuclear reactor pressure vessels, piping, and nozzles. The code requires examination of 0°, 45°, and 60° sound beam viewing from both sides of a weld. Current testing systems used to inspect pressure vessels from the outside surface employ quasi-contact techniques to couple the ultrasonic energy from a multiple transducer head into the surface of the component being tested. The transducer heads are moved across the weld and the data are recorded on magnetic tape, CRT display, pen recorder or a combination of displays. The systems are relatively slow and require several minutes to cover a one-foot section of weld. Interpretation of the recorded data requires detailed examination and is subject to human interpretation in order to measure the dimensions of the flaws found in the component.

Acoustic holography has been successfully used to characterize known defects; however, present single surface holographic techniques are quite slow. Typically these systems require between five to ten minutes to scan one square foot of weld. In addition, many holograms are required to develop an accurate interpretation of the ultrasonic reflector.

Ultrasonic arrays are currently being used with great success in the medical ultrasonic diagnostic field. These techniques primarily use the pulse-echo method of operation. The use of arrays has been proposed for industrial applications, but while several concepts have been researched, no validated system has yet to be developed. The use of ultrasonic arrays for holographic imaging has also been researched and validated, but the technology has not been carried to demonstration instrumentation.

Both pulse-echo and holographic techniques utilize acoustic waves that are directed into the material being tested and reflected from surface and subsurface defects. The energy returned from a defect is a function of its size, acoustic impedance, orientation, shape, and depth within the material. For a pulse-echo measurement the time delay and signal amplitude of the reflected acoustic waves are measured. In holographic imaging the time delay, phase and signal amplitude are used to describe the defect. It is also worthy to note that pulse transmission techniques are used in both pulse-echo and holographic displays.

For pulse-echo imaging the transmitted acoustic waves should be collimated into a defined and controlled beam of acoustic waves so that the waves can penetrate deep into the material being tested and return signal information about the size of the flaws. To achieve this effect, pulse-echo transducers are usually designed for directionality and have very small angles of acceptance to off-axis incident acoustic waves.

In contrast, holographic imaging requires the transmission of a dispersive acoustic wave. The receiving transducers are generally small in order to have a large angle of acceptance and non-directional sensitivity. The receiving transducers also must maintain the phase coherence of the reflected acoustic waves incident on the receiving transducer.

Heretofore, a successfully operable transducer array that can be used for both pulse-echo and holographic acoustic imaging has not been developed because of the seemingly mutually exclusive operating requirements outlined above. Although there are transducer arrays available today that can perform one of these scanning techniques separately, there is as yet no system that can successfully perform both pulse-echo and holographic acoustic imaging with the same linear array.

SUMMARY OF THE INVENTION

The primary object of the present invention is to overcome the limitations and disadvantages of the prior art.

An additional object of the present invention is to develop a single transducer array that can be used for both pulse-echo and holographic acoustic imaging.

A further object of the present invention is to perform high-speed non-destructive evaluation of solid materials when only one surface of the material is available for inspection.

Another object of the present invention is to develop a transmitting transducer array that transmits a collimated beam of acoustic waves that can be steered for pulse-echo imaging and a transducer array that transmits a dispersive beam of acoustic waves for holographic imaging.

Still another object of the present invention is to provide a receiving transducer that can detect normally incident acoustic waves with high sensitivity for pulse-echo imaging and a transducer that has a large angle of acceptance to acoustic waves for holographic imaging.

An additional object of the present invention is to pulse a transducer array and to sequence its signals with digital logic circuits.

These and other objects are achieved by a linear transducer array having a subarray of transmitting transducer elements disposed in a plane and along the first axis. Each element of the subarray has an elongate shape and a principal axis that is normal to the first axis. The linear array also has a subarray of receiving transducer elements coplanar with the transmitting subarray and disposed parallel to the first axis. Each element in the receiving subarray is located adjacent to a corresponding element in the transmitting subarray. For holographic imaging a removable mechanical shutter is positioned to block a predetermined portion of the length of each of the elongate transmitting elements so that a dispersive beam is generated when a relatively small number of elements in the transmitting subarray is energized.

Additional objects and features of the invention will appear from the following description in which the preferred embodiments have been set forth in detail in conjunction with the accompanying drawings.

BRIEF DESCRIPTION OF THE DRAWINGS

FIG. 1 is an isometric view of a transducer array according to the present invention.

FIG. 2 is a side elevational view, in section taken along line 2—2 of the transducer array of FIG. 1.

FIG. 3 is a top plan view, in section and broken away, taken along line 3—3 of the transducer of FIG. 2.

FIG. 4 is a diagram of the transmitting and receiving elements in the linear transducer array of FIG. 1.

FIG. 5 is a front elevational view, partially broken away, of an alternative embodiment of the present invention.

FIG. 6 is an isometric view of the transducer of FIG. 1 with a mechanical shutter in place for holographic imaging.

FIG. 7 is an electrical schematic diagram of a pulser for energizing a transmitter element in the linear array of FIG. 1.

FIG. 8 is a block diagram of the transmit and receiver steering electronics for the transducer of FIG. 1.

FIG. 9 is a table illustrating how the transmitter elements are selected by the transmit steering electronics of FIG. 8.

FIG. 10 is a timing diagram for the transmit steering electronics of FIG. 8.

FIG. 11 is an electrical schematic diagram of the pre-amplifiers for the receiver elements of FIG. 1.

FIG. 12 is an isometric view of a mechanical scanning bridge for translating the transducer array of FIG. 1 across the component being tested.

FIG. 13 is a diagram illustrating the mechanical motion and the scanning path of the transducer array of FIG. 1 as it is moved across the component by the scanning bridge of FIG. 12.

FIG. 14 is a block diagram of an alternative embodiment of the receiver steering electronics for the transducer of FIG. 1.

DESCRIPTION OF THE PREFERRED EMBODIMENTS

THE LINEAR ARRAYS—GENERALLY

FIGS. 1-3 illustrate one embodiment of a linear transducer array according to the present invention. The linear array 8 includes three subarrays: an upper subarray 10 and a lower subarray 12 of transmitting transducer elements and a medial subarray 14 of receiving transducer elements. For the purposes of identification, the term "array" herein refers to the entire transducer and the term "subarray" refers to one particular set of transducer elements. The three subarrays 10, 12, 14 are co-planar and the elements of each are disposed in parallel with the longitudinal axis (not shown) of the array. FIG. 5 depicts an alternative embodiment that includes one subarray of transmitting transducer elements 12 and one subarray of receiving elements 14. The transducer arrays of FIGS. 1 and 5 are used for pulse-echo acoustic imaging and consist of one hundred and twenty transmitter and one hundred and twenty receiver elements. When holographic imaging is performed, the transducer array of either FIGS. 1 or 5 is used with a mechanical shutter as shown in FIG. 6. As described below, each array can accommodate the criteria for both holographic and pulse-echo operation.

THE SUBARRAY OF TRANSMITTING ELEMENTS

Referring to FIG. 1, the upper subarray 10 of transmitting transducer elements is cut from a plurality of piezoelectric crystals 16 which are adhesively bonded to a backing 18. The crystals are cut to form rectangular, elongate elements. Each element of the subarray has a principal axis normal to the longitudinal axis of the array. The piezoelectric crystals are fabricated from either lead zirconate titanite (PZT) or lead metaniobate ($PbNb_2O_6$). The backing material 18 is fabricated from a non-conductive acoustic wave-absorbing material such as epoxy resin loaded with aluminum oxide. This material is used because the transmitting subarray need not be critically damped.

The purpose of the dimensioning and positioning of the transmitting elements is to achieve the desired sound beam configurations described below. The sound field generated from a single transmitting element is collimated in the longest dimension and dispersive in the narrowest dimension. It should be appreciated that this type of beam from a single element is ineffective for the inspection of heavy section steel materials. However, when a number of these transmitting elements are ganged together and pulsed simultaneously or in a programmed sequence, the energy produced by individual elements phase-reinforces to produce a collimated beam.

Each transmitting transducer element 16, FIG. 2, is connected by an individual lead 19 to a transmitter circuit card 20. In addition, each transmitting transducer element is grounded by a ground board 24 fabricated from a conductive material. The ground board overlaps the transmitting circuit card and projects down the front of the subarray to touch the upper frontal surfaces of each transmitting transducer element.

Each lead 19, FIG. 2, from each transducer element 16 is connected through the transmitter circuit card 20 to a pulser 22. The pulsers are described below in connection with FIG. 7. To produce a scanning sound field, selected groups of transmitting elements are sequentially pulsed by the pulsers in a predetermined pattern. To generate an angle beam with the array, the time relationship of the initiating pulse to each element is controlled by the pulser to provide a phase-reinforcement which will propagate as an angle beam in the component being tested. The time relationship to individual elements is controlled by digital logic sequencing from a computer as described below.

The lower subarray 12, FIG. 2, of transmitting transducer elements is constructed and operates in the same manner as the upper subarray 10 described above. Thus, the redundant details of the lower subarray are not repeated. Each pulser 22 drives a corresponding element in each subarray simultaneously. That is to say, both transmitting transducer elements 2, 2', FIG. 1, for example, are driven together.

THE SUBARRAY OF RECEIVING ELEMENTS

The medial subarray 14, FIG. 1, of receiving transducer elements is cut from a plurality of piezoelectric crystals 28. Each element in this subarray has a generally rectangular shape and is located adjacent to a corresponding element in the upper and lower transmitting subarrays. The transducer elements are each dimensioned to be no larger than the length of two times the wavelength of the acoustic waves incident on the array.

This dimensioning insures that the subarray of receiving transducers has a large angle of acceptance to off-axis incident acoustic waves.

The piezoelectric crystals 28 in the medial subarray 14 are adhesively bonded to a non-conductive acoustic wave-absorbing backing 30. The backing can be fabricated from the same material as the transmitting subarray backing 18 or some other backing material that provides both acoustic absorption and impedance matching. The front surfaces of the receiving transducer elements are grounded by an electrically conductive lead 38, FIG. 2, which is located between the upper subarray 18 and the medial subarray.

Referring to FIGS. 2 and 3, each receiving transducer element 28 is attached by a lead 34 to an individual preamplifier 36. The preamplifiers are described in detail below in connection with FIG. 11. The backing 30, FIG. 3, for the receiving piezoelectric crystals 28 is drilled with a plurality of holes through which the leads 34 pass. The entrance to each hole is also chamfered to permit the entry of the welded portion of each lead attaching it to the rear surface of the receiving crystals 28. The backing is adhesively bonded to the receiving subarray by a thin layer of epoxy resin 32.

FABRICATION OF THE ARRAY

The linear transducer array 8, FIG. 1, is fabricated after the transmitting and receiving crystals 16, 28 are adhesively bonded to the associated backings 18, 30, and the signal leads 19, 34 are attached to the rear surfaces of the crystals. Thereafter, the three subarrays 10, 12, and 14 are bonded together to form a flat transducer surface with parallel sides. Next, the piezoelectric crystals are cut with a slicing saw (not shown). The slicing saw cuts the crystals into separate, individual elements as illustrated in FIG. 3. Each element in the three subarrays is isolated electronically and acoustically from its adjacent neighbors. This provides the means for electronically steering the axis of propagation of the sound field and the axis of maximum sensitivity.

Referring to FIG. 5, the present invention also contemplates the use of one subarray of transmitting transducer elements 12 in combination with a subarray of receiving transducer elements 14. The two subarrays are constructed and operate in the same manner as described herein. When two subarrays are used to form the linear transducer of the present invention, the transducer should be rotated slightly in order to insure that a large return signal is reflected back to the array when nearby materials are imaged.

In one design the upper and lower subarrays 10, 12, FIG. 1, are each fabricated from six one-inch long piezoelectric crystals and each subarray has an operating frequency of 2.3 MHz. This frequency is based on the clock frequency used in the transmit steering electronics, FIG. 8. The large crystals are cut to form one hundred and twenty elements. Each transmitting element has a width of 0.05 inches and a height of between 0.45 and 0.5 inches. The center-to-center spacing between the principal axes of the elements is 0.05 inches. The size of the transmitting elements is chosen to provide a center-to-center spacing when imaging steel of one $\lambda$ for the shear mode of operation and $\lambda/2$ for the longitudinal mode of operation. The subarray of receiving transducer elements is also fabricated from six one-inch long piezoelectric crystals. The crystals are cut to form one hundred and twenty elements. Each element has a height of between 0.09 and 0.1 inches and a width of between 0.04 and 0.05 inches. The receiver subarray when mated with the other subarrays is 0.1 inches wide by 6 inches long, and each transmitting subarray is 0.5 inches wide by 6 inches long. The slicing saw forms one hundred and twenty elements in the three subarrays, and the saw cuts are about 0.01 inches wide.

The size of the receiver elements is a compromise between the requirements for holography, sensitivity, angle of acceptance, beam steering, and manufacturing. The receiver elements are designed to be as small as possible in order to provide phase coherence for holographic reconstructions and to have a wide angle of acceptance. It has been observed that for pulse-echo imaging a small receiver element is not as critical to echo normalcy as a large receiver element and a small element can detect incident energy over a broad angle with high efficiency. One feature of piezoelectric materials is that the receiving efficiency is not a linear function of element size. Thus, a very small receiver coupled with a preamplifier 36 can provide signal voltages as large as receiving elements twenty times larger in size.

OPERATION OF THE ARRAY

In mathematical terms the radiation pattern transmitted from each transmitting transducer element in either mode of operation is given by the following equation:

$$F(\theta) = f_1(\theta) \frac{\sin^2\left[\frac{N\pi d}{\lambda}(\sin\theta - \sin\theta_o)\right]}{N^2 \sin^2\left[\frac{\pi d}{\lambda}(\sin\theta - \sin\theta_o)\right]} \quad (1)$$

where $f_1(\theta)$ is the radiation pattern of each element, $\theta$ is the angle from normal as shown in FIG. 1, $\theta_o$ is the angle to which the array is steered, N is the number of elements and d is the center-to-center spacing, FIG. 4.

From elementary theory the pattern of each element is $$f_1(\theta) = \frac{\sin^2\left(\frac{\pi a}{\lambda}\sin\theta\right)}{\left(\frac{\pi a^2}{\lambda}\right)\sin^2\theta} \quad (2)$$

where a is the width of each element, FIG. 4.

Thus, the total pattern becomes $$F(\theta) = \frac{\sin^2\left(\frac{\pi a}{\lambda}\sin\theta\right)}{\left(\frac{\pi a}{\lambda}\right)^2 \sin^2\theta} \cdot \frac{\sin^2\left[\frac{N\pi d}{\lambda}(\sin\theta - \sin\theta_o)\right]}{N^2 \sin^2\left[\frac{\pi d}{\lambda}(\sin\theta^2 - \sin\theta_o)\right]} \quad (3)$$

$$= f_1(\theta) f_N(\theta)$$

where $f_N(\theta)$ is the array factor.

Some properties of the array factor, $f_N(\theta)$, are $$f_N(\theta) = 1 \text{ for } \sin\theta = \sin\theta_o \pm \frac{n\lambda}{d}. \quad (1)$$

These angles define the principal maxima or grating lobes.

$$f_N(\theta) = 0 \text{ for } \sin\theta = \sin\theta_o \pm \frac{n\lambda}{Nd}. \quad (2)$$

These angles define the zeros between grating lobes and there are $N-1$ of them.

(3) Since $f_N(\theta) \geqq 0$, there is a relative maximum between each pair of zeros. Therefore, there are $N-2$ subsidiary maxima between adjacent principal maxima.

The size of the ultrasonic beam transmitted by the array 8, FIG. 1, is a function of the size of the transmitting elements, the frequency of operation of the system, and the medium into which the beam is propagating. The linear array 8 operates at 2.3 MHz with either a water standoff or a thin water-gap couplant (not shown). The acoustic energy is fluid-coupled from the transmitting elements into the component being inspected. For the pulse-echo mode of operation, the transmitting elements propagate a steerable, collimated beam. The transmitting elements are energized in a pattern that overlaps and is sequenced step-wise down the array by the pulsers 22. Sixteen individual transducer elements in each subarray are energized in each cycle to develop either the zero or angle beams required for inspection. Each group of sixteen elements overlaps the previously energized group by elements by eight elements. Each pulser 22 drives the corresponding elements in both the upper and lower subarrays 10, 12 simultaneously.

The receiving transducer elements in the medial array 14, FIG. 1, are used to detect the acoustic beam reflected from a subsurface defect. To receive the acoustic waves propagated by each group of sixteen transmitting elements, a group of eight alternating receiving elements is sampled by the computer as described below. For example, if transmitting elements 1–16, FIG. 1 inclusive, are pulsed to generate an acoustic beam, then receiving elements 1, 3, 5, 7 . . . 15 are sampled. Alternating receiving elements are used in order to increase the number of descrete angles that the array can accept.

In the holographic mode of operation a dispersive beam of acoustic waves is transmitted from the array. The source of the sound beam is made as small as possible—consistent with the amount of power required to penetrate the heavy steel components being inspected. A beam having a divergence of at least 40° measured with respect to the axis of propagation is preferred. Referring to FIG. 6, in the preferred embodiment, only a small number of transmitting elements are driven at one time. Typically, only five or fewer transmitter elements are energized at one time. To reduce the source length, a mechanical shutter 40, 40', FIG. 6, is introduced to cover all but the desired fraction of each transmitting element as illustrated in FIG. 6. The shutter consists of two leaves that are positioned in front of the transmitting transducer subarrays by a shutter positioner 42. The positioner is of known construction and causes the leaves to move into position for holographic operation and to be removed from in front of the array for pulse-echo operation. The leaves of the shutter can be fabricated from a sheet of cork sandwiched between two sheets of thin steel shim.

When the mechanical shutter is in place, it reduces the aperture size of the transmitting elements. In FIG. 6 the upper leaf 40' completely masks the upper subarray 10 and the lower leaf 40 is positioned to expose a length of each element equal to the width of the elements that are pulsed together in the lower subarray 12. In other words the shutter position and the combined width of the 3–5 pulsed elements cause the source of the sound beam to have the effective shape of a small square. The holographic scan is achieved by electronically sequencing the small group of selected elements in the array as described below. The shutter does not change the impedance of the transmitting transducer array and so no modification of the pulsers 20 is required for holographic scanning.

When the acoustic waves are reflected back to the array 8 in the holographic mode of operation, the waves are detected by one single receiving element in the medial array 14. This receiving element is one that is centrally located within the selected group of transmitter elements. For example, if the transmitter elements 21, 22 and 23, FIG. 1, are energized, then receiving element 22 is sensed. Only one of the receiving elements is sampled so that the array has non-directional sensitivity and a large angle of acceptance to the incident acoustic waves reflected by the component being tested.

THE TRANSMIT ELEMENT PULSER

The transmitting transducer elements 46 in the upper and lower subarrays 10, 12, FIG. 1, are driven by high voltage pulser circuits. Referring to FIG. 7, each pulser excites the transmitting elements to a voltage level of between 300 and 400 volts. In the preferred embodiment there are one hundred and twenty pulsers that are connected to the one hundred and twenty sets of two transmitting elements. Each pulser circuit, FIG. 7, is a low impedance driver designed to drive a long cable 48 and two transmitting elements 46 effectively. The circuit includes a tank circuit comprising an inductor L1, a capacitor C2 and a resistor R4. These circuit elements in combination with transistor Q1, which is a 2N3501 transistor, generates a sinusoidal voltage from the square wave TTL input from the switching matrix 59, FIG. 8. The sinusoidal output signal from the tank circuit and transistor Q1 appears at the input to transistor Q2 and Q3 and has a frequency of 2.3 MHz. Vbb is a supply voltage for the circuit and resistor R9 and capacitors C1 and C3 are circuit elements used for decoupling the power source Vbb. Resistor R6 is also a coupling resistor.

The pulser circuit, FIG. 7, also includes a plurality of parallel push-pull drivers that serve as a transition between the tank circuit and the transformer X1. These drivers transpose the high impedance from the tank circuit into an impedance that permits the effective driving of the transformer X1, the cable 48, and the transmitting elements 46. The drivers are a network of emitter followers. Transistors Q2, Q4 and Q6 are 2N3501 transistors and take the positive portion of the sinusoidal voltage signal from the tank circuit. Transistors Q3, Q5 and Q7 are 2N3637 transistors and take the negative portion of the sinusoidal voltage from the tank circuit. The push-pull drivers are connected to a step-up transformer X1 that drives the transmitting elements through the cable 48. The transformer has a ratio of 4 to 1 and steps up the circuit voltage while maintaining the impedance sufficiently low so that the transmitter elements and the cable are effectively driven.

TRANSMIT AND RECEIVE ELECTRONICS—GENERAL

The beam steering electronics circuit is illustrated in FIG. 8. Functionally, the system is controlled by a computer (not shown) which controls both the mechanical and electronic beam position and the beam angle. The computer steering commands include selected beam angle, element grouping, and number of cycles to be applied to the transmitter elements by the steering electronics.

For pulse-echo operation, the computer (not shown) instructs the transmit steering electronics, FIG. 8, to pulse a selected group of sixteen transmitter elements in the upper subarray 10, FIG. 1 and also in the lower subarray 12. The transmitting elements in the upper and lower subarrays are each driven together by a separate pulser 22, FIG. 8. The time delay established between each of the transmitting transducers determines the propagation angle of the sound beam. In the preferred embodiment a 37 MHz oscillator is used as a reference clock. The basic time period between clock pulses in 1/f or 27 nanoseconds, thus the transmit delay periods between transducer elements are all a function of $F(t) = N \times 27$ nanoseconds as established by the "m" divide counter 55. A 16 bit shift register 57 provides a time input to the switching matrix 59 which in turn selects the pulsers 22 that will be used to launch the ultrasonic beam from the array.

The basic frequency of the driving waveform for the pulsers is 2.3 MHz as determined by the clock frequency and the m divide counter 55. The number of cycles applied to the pulsers and in turn to the transmitting elements is determined by the m divide counter 55. For the pulse-echo mode of operation a selected pulser is typically excited for 1 to 4 cycles. For the holographic mode of operation a selected pulser is excited for periods of between 5 to 20 cycles. The switching matrix 59 establishes either positive or negative beam angles in either the pulse-echo or the holographic modes of operation. In one embodiment actually under construction the available delays provide for a total of forty-nine selectable angles including fifteen sheer and nine longitudinal angles in both the positive and negative directions plus the zero mode.

Sixteen transmitting elements are used in the pulse-echo mode of operation to provide a sound beam that has approximately the same dimensions as a beam obtained from a 0.9 by 0.9 inch crystal. The scan across the array is achieved by sequencing successive groups of sixteen transmitting elements in each subarray. Each group overlaps the prior group by eight elements. Each pulser energizes one element in the two subarrays because the upper and lower corresponding elements in each subarray are electrically connected together. In normal operation the apparatus sequences the transmitting elements in successive groups with a beam orientation of zero degrees. Next the apparatus sequences the beam across the array at 45° and then at 60°. Upon completion of the three scans the cycle is repeated at a new location on the component until a full inspection of the area being scanned is completed. The pulse rate of the system is based upon the longest path length requirements for the sound beam. In normal operation the 60° angle scan requires the slowest repetition rate. The speed of travel of the array across the mechanical bridge, FIG. 10, is established to insure a minimum of 50% indexing of the sound beam in both the X and Y scan directions.

In particular, the transmitter elements 1 through 16 inclusive in each subarray, 10, 12, FIG. 1, are used to generate the sound beam for the first pulse in a scan. The second pulse in the scan drives elements 8 through 24 and the third pulse drives elements 16 through 32. The steering electronics thereby sequences across the array in successive overlapping pulses.

For holography the array is scanned in a similar manner but the number of elements is reduced in order to develop a divergent sound beam. In addition, the shutters 40, 40', FIG. 6, are positioned in front of the transmitting elements. It has been observed that energizing between three to five transmitting elements is sufficient to project an adequate beam for holographic imaging. To develop a beam that is symmetrical in both the X and Y directions, the mechanical shutters are placed in front of the array to block off the array and develop a square transducer configuration. Beam steering in holographic imaging is achieved by selecting the time delay triggering of the individual pulsers 22. The array sequencing in holographic transmission differs in that the group of elements being energized is advanced only by a single element at a time. That is to say transmitter elements 1, 2, and 3 are first energized; then elements 2, 3, and 4, and thereafter elements 3, 4, and 5, etc.

The major function of the receiver steering electronics, FIG. 8, in the pulse-echo mode of operation is to extract return signals from eight receiving elements in the array, subject each of the signals to an appropriate time delay depending on the beam angle, and sum the delayed signals together to form a composite output signal. Separate receiver preamplifiers 36 are used for each of the receiver elements 28. The same receiving transducer elements 28 are used in both the pulse-echo and the holographic modes of operation. For pulse-echo operation eight receiver elements are used for each block of sixteen transmitting transducer elements that are energized. As an example, receiver elements 1, 3, 5, 7, 9, 11, 13, and 15 are used when transmitter elements 1 through 16 inclusive are pulsed. Since the time delays in the receiving electronics are the reciprocal of those in the transmitting electronics, the receiver steering electronics, FIG. 8, handles the signals received by the array in an entirely different manner. For any beam angle the signals impressed on the receiver elements 28 are amplified by the preamps 36, 78 and passed to an A to D converter 62. The digitized signals are then delayed, reconverted into analog waveforms and summed to reconstruct the signal. Once the signals are summed, the signals are transmitted as output signals from the electronics to a display system (not shown) for further processing and imaging.

In the holographic mode of operation only a single receiving transducer element 28 is used at one time. The switching section 64, FIG. 8, selects the center element adjacent to the transmitting group as a receiver. This selection is illustrated in FIG. 6. The sequencing of receiving elements is a simple progression across the receiving subarray 14. For example, when transmitting elements 3, 4, and 5 are energized, the output of receiving element 4 is detected and when elements 4, 5, and 6 are driven, receiving element 5 is selected. The holographic signal is amplified and passed to the computer (not shown) for appropriate phase correction prior to being displayed.

TRANSMIT STEERING ELECTRONICS—SPECIFIC

The array of transmitting transducers includes two subarrays 10, 12 each comprising one hundred and twenty equally spaced apart transducer elements 16. The function of the transmit steering electronics, FIG. 8, is to select sixteen adjacent transmitting elements in each subarray and to apply a phase controlled driving signal to each element. The transmit steering electronics provides either a signal pulse driving function or a burst of pulses having a pulse repetition rate equalling the natural frequency of the array. Beam steering is accomplished by programming a predetermined time delay in the firing order for each transducer element. For holography the transmit steering electronics selects and pulses on command any of the adjacent elements in the array.

Each subarray 10, 12 is subdivided into sixteen element blocks and each block is further divided into element sub-blocks. The table illustrated in FIG. 9 describes the firing of each transmitting element as a function of the block and sub-block selected, delay time and sign of the angle selected (plus or minus). Depending on the beam angle selected, each delay time is separated from its neighbors by a multiple of twenty-seven nanoseconds. In addition, delay 1 occurs before delay 2 and so forth. When the pulse echo mode of operation is selected, the holographic sub-blocks are not used and all sixteen elements in a block are energized according to the delay times. For example, to energize transmitting elements 34, 35 and 36, FIG. 9, in the holography mode with a plus angle, the computer issues a code for the proper angle, a plus angle signal, a holography signal, and the appropriate block and sub-block codes. The block and sub-block codes are obtained from the table illustrated in FIG. 9. In particular, block 4, subblock 10 or block 5, sub-block 2 addresses the three element group in the subarray.

To provide the basic time delay for the transmit steering electronics, FIG. 8, a 37 MHz clock signal is used. This clock signal has a twenty-seven nanosecond period and is sent to a pre-settable, divide by "n" counter 66. The output of the "n" counter is a clock pulse having a period determined by the value at its preset inputs. If the counter outputs a pulse at count 16, for example, and the counter will count four 37 MHz pulses before the output pulse occurs. Since the counter counts four 37 MHz pulses before outputting a pulse, this output pulse will have a period of $(4\times27)=108$ nanoseconds.

The output from the divide by n counter 66, FIG. 8, is used to clock a 16 bit shift register 57. Each of the sixteen outputs from the shift register is thereby delayed from the preceding output signal by a time equal to the period between clock pulses from the divide by n counter 66. Sixteen different delay periods can therefore be obtained merely by changing the value applied to the preset inputs of the divide by n counter, representing sixteen different beam angles.

No data is shifted through the shift register 57 until a START XMIT pulse sets the XMIT FLIP-FLOP 67. The true state of the XMIT FLIP-FLOP output propagates down the shift register with a velocity determined by the output of the divide by n counter 66.

The sixteen output lines from the shift register 57, FIG. 8, are each connected to a circuit comprised of a sync gate 69 and a divide 16 counter 70. The divide 16 counter is used to divide the 37 MHz frequency signal down to 2.31 MHz, which is the repetition rate of the signal sent to the output pulsers 22. The sync gate 69 samples three signals: the corresponding shift register output, the output of its associated divide by 16 counter and a "carry" sent to it by the previous SYNC GATE. The proper combinations of these signals will turn the divide by 16 counter on and off at predetermined times, generating a string of 2.31 MHz output pulses with the correct timing relationship with the other fifteen outputs to accomplish beam steering.

FIG. 10 illustrates the timing diagram of the transmit steering electronics. The inputs and outputs of SYNC GATES 69 are labelled on FIG. 10 as follows:

SR—Shift register output
C—"carry" input
D—2.31 MHz delayed pulse
EN—count enable output to divide 16 counter By way of example the second transmitter channel, FIG. 8, which includes the second output from the shift register 57, the SYNC GATE 69, the divide 16 counter 70 and the second data input line $D_2$ to the switching matrix 59 operates in the following manner. The $EN_2$ output initially goes true when the $C_2$ and $SR_2$ inputs are true. From the timing diagram FIG. 10, it can be seen that the $C_2$ input is always true before the $SR_2$ input goes true. This means that the rising edge of the $EN_2$ output, a transition from false to true, is coincident with the rising edge of the $SR_2$ input. In other words, during turn-on the SYNC GATE 69 acts as though there is a path from the $SR_2$ input to the $EN_2$ output. One 37 MHz clock pulse later, the first 2.31 MHz pulse appears on line $D_2$.

During each falling edge of the 2.31 MHz pulses, the state of the $C_2$ input is tested. If $C_2$ is true, then another 2.31 MHz pulse will occur. On the other hand, if $C_2$ is false, the divide 16 counter 70 is disabled and cannot be re-enabled until the $SR_2$ input has another false-to-true transition.

It can be seen from the block and timing diagrams, FIGS. 9 and 10, that the first channel's 2.31 MHz delayed output pulses (D1) pass through the divide m (pulses select) counter 55 and reset the XMIT FLIP-FLOP 67 at the proper time. This resets the first channel's carry input ($C_1$). In this regard, channel 1 is different from the other 15 channels.

The divide by m (pulses select) counter 55 is preset to the number of output pulses desired. As the 2.31 MHz pulses are output from the divide 16 counters, the pulses are counted down from the preset number in the divide m counter. When the divide m counter reaches a count of zero, the XMIT FLIP-FLOP 67 is reset and a false condition will therefore propagate down the shift register 57 turning off the divide 16 counters.

The sixteen outputs from the divide 16 counters 70 along with the fourteen block and fourteen sub-block select lines, a holography/pulse echo select line from the computer and an angle sign (+/−) line from the computer are sent to the switching matrix 59, FIG. 8. The switching matrix is connected to each of the one hundred and twenty transmitter pulsers 22 by individual output lines. These output lines are enabled when the conditions of FIG. 9 are met. The switching matrix selects the designated sixteen transmitting transducer elements according to FIG. 9 and establishes the desired firing order and incremental delay. The inputs to the switching matrix illustrated in FIG. 10 are two pulses having a 54 nanosecond delay.

The switching matrix 59, FIG. 8, drives the pulsers 22, FIG. 8, in the manner described above. The switching matrix is connected to transistor Q2, FIG. 7 in each of the pulsers and provides the input pulses as illustrated. The power supply 73, FIG. 8 is $V_{BB}$, FIG. 7. Each pulser is connected to two transmitting transducer elements 16, FIG. 8, that simultaneously radiate acoustic waves.

To generate ultrasonic signals for holographic imaging, the switching matrix 59, FIG. 8, receives computer steering commands through the block decoder 71 and the holographic sub-block decoder 72. These commands prescribe the grouping of adjacent transmitter elements that will be driven by the circuit. An oscillatory burst of 2 MHz CW is developed across the transmitter elements with phase relationships as required to develop the proper beam angle. The phase shift between the elements is established by the shift register 57. The switching matrix 59 connects each of the transmitter elements 16 to a prescribed output tap of the shift register thus exciting each transmitter element at a fixed phase delay with respect to its lowest neighbor in the firing order. The firing order, depending on whether a + or − angle is required, is specified by the sequence of delay times, FIG. 9. The n counter 66 generates a train of pulses that is picked off of the appropriate shift register taps and applied to the element pulsers 22 by the switching matrix 59. The selected pulsers convert the pulse train from the shift register into a high voltage sine wave that drives the transducer elements.

RECEIVE STEERING ELECTRONICS—SPECIFIC

The purpose of the receiver steering electronics, FIG. 8, is to gate the signals detected from a prescribed group of receiving transducer elements 28 onto a common output line through appropriate time delays. The switching section 64, FIG. 8, in the pulse-echo mode receives computer steering commands to select eight of the one hundred and twenty receiving transducer elements 28 and to gate the signals sensed by these elements onto the eight output lines from the switching section. Depending on the block of transmitting elements selected for pulsing, the computer selects the odd numbered receiving elements within the identical numbered group in the receiving subarray.

In the holographic mode of operation the switching section 64, FIG. 8, selects one of the one hundred and twenty receiving elements 28. The number of the selected receiving element is in the middle of the group of numbers identifying the transmitting elements being energized. The signal received by that selected receiving element is amplified by a holography preamplifier 75 and is passed through the output data selector 77 as the composite output signal.

In the pulse-echo mode of operation signals from the eight selected receiver elements 28 are preamplified, envelope detected, and input in a prescribed order into eight Analog to Digital (A-D) converters 62, FIG. 8. The preamplifier 78 includes an envelope detector. The envelope amplitude is digitized into a 3-bit word (eight levels of quantization) at an update rate of 54 nanoseconds and is input to a shift register described below. The process is performed simultaneously for each of the eight selected outputs from the switching section 64. The digital envelope data is clocked through the shift register at 55 nsec clocking intervals. The shift registers are organized into a serial input, parallel output mode so as to constitute a digital delay line with multiple output taps.

The shift registers delay the eight output signals from the switching section 64, FIG. 8, by specific predetermined multiples of 54 nsecs. Since each shift register or delay line channel is identical, only one need be described. Each delay line channel includes a 128×4 bit random access memory (RAM) 79, a 4-bit latch 80, and a RAM Address Encoder 81. An 18.5 MHz square wave having two states each 27 nsecs long is used as the basic timing signal. For the purposes of description one state is hereinafter identified as WRITE and the other state as READ.

The RAM Address Encoder 81, FIG. 8, contains two 7-bit binary counters. One counter is hereinafter identified as the Write counter and the other as the Read counter. One 7-bit address bus connects the encoder 81 to the RAM 79. When WRITE on the clock is true, the Writer counter is connected to the bus, and when READ is true, the Read counter is connected to the bus. Therefore, the RAM 79 is alternately addressed by the Write counter and then the Read counter.

The RAM 79, FIG. 8, writes the 4-bit word on its DATA input lines from the A-D converter 62 into the location specified by the Write Counter or puts the contents of the location specified by the Read Counter into its DATA out lines to the 4-bit latch 80 depending on whether WRITE or READ is true. The output latch is strobed when READ is true, so data on the RAM DATA out lines is held constant for one full cycle, until the next time READ becomes true. Data on the latch 90 outputs are passed through a Digital to Analog converter 82 and then summed in a summer 83 with the signals from the other seven receiver delay channels.

At the end of the READ signal both the Write counter and the Read counter in the RAM Address Encoder 81 are incremented by one. The operation of the circuitry described so far is as follows:

1. A 4-bit word from the A–D converter 62 is written in location w in the memory.
2. A 4-bit word is read from the location r in memory and held in the 4-bit latch 80 from which this word is sent to a D-A converter 82 and summed with the seven other signals.
3. w and r are incremented by one.
4. Steps 1, 2 and 3 are repeated until either w or r equals 127, the last location in memory. When this occurs, the next incremental pulse causes either w or r to be reset to 0 depending on which equals 127. The other is merely increased by one, as is normal.
5. Steps 1, 2, 3 and 4 repeat endlessly.

The total delay time in each receiver delay channel is the time between when a signal enters the Analog to Digital converter 62 and when the signal appears at the output of the Digital to Analog converter 82. The total time delay is in direct proportion to the number of locations in memory between w and r. In fact it can be shown that $$t_d = \begin{array}{ll} (2[w\text{-}r] + 1) & (27 \text{ nsec}) : w > r \\ (2[w\text{-}r] + 257) & (27 \text{ nsec}) : w < r \end{array}$$

where $t_d$=total delay time

To establish the proper delay time it is necessary to assign the proper quantity (w−r) in the Read and Write counters in the RAM Address Encoder 81. The magnitudes of w and r are unimportant, and if r is preset to 0, then the delay time is strictly a function of what value of w is preset into the Write counter.

All of the outputs from the D-A converters 82 are summed together in an analog summer 83 and are placed on a pulse echo data line. The output data on this line is the sum of the signals from all eight receiving transducer elements after the signals from each element have been delayed in time by the shift register - delay line channels. In the pulse echo mode this data then passes through the output data selector 77 and becomes the composite output signal.

PRE-AMPLIFIER CIRCUIT

Each receiving transducer element 28 in the medial array 14, FIG. 1, is connected to a pre-amplifier 36 as illustrated in FIG. 11. This circuit isolates the receiving transducer elements from the capacitance of the cable 84 connecting the element to the switching section 64, FIG. 8. The pre-amplifier circuit includes a 2N3904 transistor Q3 that forms a buffer amplifier. Each buffer amplifier is located adjacent to its receiving transducer element on the array. The buffer amplifier both receives power and sends back amplified signals through a single conductor 84. The output current from the transistor Q3 drives a cascode amplifier which includes transistor Q4. Transistor Q4 is also a 2N3904 transistor which in turn drives a medium Q tank circuit comprising capacitor C3 and inductor L2 which is tuned to 2.3 MHz.

MECHANICAL SCANNING BRIDGE

The transducer array 8, FIG. 12, consisting of the two transmitting subarrays 10, 12 and the receiving subarray 14 is maneuvered by a mechanical scanning bridge 86, FIG. 12. The motion of the transducer array is controlled by a computer (not shown) which defines all of the standard X and Y movements of the array, selects the speed of travel and maintains exact position information so that the transducer coordinates can be synchronized with the signals obtained from the apparatus. During the pulse echo mode of operation the array 8 travels across the carriage in the X direction in ten seconds and indexes along the Y direction in five seconds so that approximately fifteen seconds is required for each cycle of motion. These motion cycles are illustrated in FIG. 13. The embodiment presently under construction is capable of manipulating the transducer array over an inspection area that is 24 in. wide and 60 in. in length. This embodiment is primarily for ultrasonically imaging a weld 87 in a steel plate 88.

The array 8 is driven along the X axis by a high-speed stepping motor 90 and along the Y axis by a high-speed stepping motor 91. The stepping motors are mechanically coupled to the scanning bridge with timing belts. Each pulse from the computer drives a stepping motor to provide either an X or Y motion of 0.002 in. The array 8 is connected by cables 48, 84 to a stationary housing 93 which contains portions of the pulsers 22, FIG. 7, and the pre-amplifiers 36, FIG. 11. In particular, transistors Q1 and Q3, FIG. 7, are located in housing 93 as well as transistor Q4, FIG. 11. Transistor Q3 is physically connected to array 8 and moves with the array during acoustic scanning.

The acoustic array 8, FIG. 1, the associated electronics, FIG. 8 and the scanning bridge 86, FIG. 12, are designed to produce a steered, collimated sound beam to illuminate an area being examined. Scanning is performed by using a combination of beam steering and mechanical positioning of the ultrasonic array. Ultrasonic data from the object 88, FIG. 12, being scanned is processed into a composite output signal, FIG. 8. To comply with the ASME boiler and pressure vessel code cited above, the apparatus provides a zero degree, a 45-degree and a 60-degree sound beam to scan the weld 87, FIG. 13. In the pulse echo mode of operation, the array 8 is translated along the path indicated in FIG. 13 by the mechanical scanning bridge 86 described above. It should be noted that steering the acoustic beam is independent of mechanical motion of the array.

A typical sequence of scanning in the pulse echo mode of operation is as follows: First, the array 8 is positioned in one corner of the mechanical scanning raster, FIG. 13, and the first set of sixteen transmitting transducer elements is driven with zero phasing. The sum of the video signals received from the selected receiver elements is gated onto the composite output line, FIG. 8. Thereafter, transmit pulses with zero phasing are applied to the second group of sixteen transmitting elements. This second group overlaps the previous group by eight elements. The sum of the signals detected by the second group of receiver elements is gated onto the composite output line. This sequence with zero degree phasing is repeated for all of the transmitting elements in the array 8.

After the entire transducer array 8 is scanned at zero degree phasing, the computer (not shown) commands the steering electronics, FIG. 8, to shift the angle of beam transmission to 45 degrees and the groups of sixteen transmitting elements are driven in sequence with that phasing. Thereafter the beam angle is shifted to 60 degrees and the groups of sixteen transmitting elements are pulsed with that phasing. After the entire transducer array 8, FIG. 13, has been scanned from one end to the other with phasing of zero degrees, 45 degrees and 60 degrees, the computer mechanically moves the array forward for a predetermined distance using the scanning bridge 86, FIG. 12. The above described scanning sequence is repeated at this new position. When that scanning is completed, the bridge as controlled by the computer moves the array to a new position and the scanning sequence is repeated again. This process is repeated until the entire volume of the weld 87 is scanned. The bridge as controlled by the computer physically moves the array along the path illustrated in FIG. 13.

If the composite output signal indicates that the weld contains a flaw or contains an area of unusual reflectivity, the array 8 is steered to a position to achieve maximum acoustic response from the area of interest. Once the response is established, the area is scanned for an ultrasonic hologram. First, the two leaves 40, 40' FIG. 6, of the shutter are positioned in front of the transducer array 8. The leaf 40' completely covers one of the transmitting transducer subarrays and the second leaf 40 covers a predetermined fraction of the length of each of the transmitter elements. In FIG. 6 the leaf 40 is moved up to a position so that effectively a square transmitting element is formed by the three transmitting elements which are pulsed together. The grouping of three elements is sequenced across the array to scan the area. To detect the reflections a single element of the received array is selected. This element is centrally located between the three transmitting elements and is sequenced with them. The signals detected by the single receiving element are amplified by the preamps 36, 75 and pass out of the receiver steering electronics, FIG. 8, through the output data selector 77. These signals are stored by the computer for subsequent reconstruction into a hologram.

ANALOG DELAY LINE FOR RECEIVER ELECTRONICS

FIG. 14 illustrates an alternative embodiment of the receiver electronics for the transducer array of FIG. 1. The receiving elements 28 in the array 14 are connected in parallel to the switching section 64 described above in connection with FIG. 8. In this embodiment there is an analog channel for each receiving element that contributes to the composite output signal. In FIG. 7 only two channels are illustrated; however, a plurality of parallel channels is intended.

The switching section 64 connects the output signals from the preamplifiers 36 to the analog delay lines 101, 101' as commanded by the computer (not shown). Each analog delay line 101 is a distributed constant analog delay line or lumped constant delay line of known construction. The delay line has one input and an output with a multiple of taps. The taps of the analog delay line are connected to an analog multiplexer 102. The multiplexer selects the total amount of delay ($\Delta t$) by choosing the appropriate delay line combination. The computer (not shown) sends to the analog multiplexer a digital beam angle address and the multiplexer, acting as a switching network, chooses the appropriate delay line combination. The output of each analog multiplexer is connected to a summer 83 which is described above.

In operation the number of active receiver elements 28 are selected by the computer and signals from these elements are switched by the switching section 64 into the analog delay lines 101, 101'. An appropriate amount of time delay is given to each signal depending upon the beam angle being used. In the preferred embodiment discrete time delays in multiples of 27 nanoseconds are used. The analog multiplexers 102 pick the signals off of the appropriate delay line taps and the delayed signals are added in an analog summer 83 to produce a composite output signal.

Thus, although the best modes contemplated for carrying out the present invention have been herein shown and described, it will be apparent that modification and variation may be made without departing from what is regarded as the subject matter of the invention.

What is claimed is:

1. A linear transducer array for both pulse-echo and holographic acoustic imaging, comprising:
  (a) a linear subarray of transmitting transducer elements disposed in a plane and along a first axis, each element of the subarray being elongate and having a principal axis normal to the first axis;
  (b) a linear subarray of receiving transducer elements co-planar with the transmitting subarray and disposed parallel to the first axis, each element in the receiving subarray being located adjacent to a corresponding element in the transmitting subarray; and
  (c) a removable mechanical shutter adapted to block a predetermined portion of the transmitting elements so that a dispersive acoustic beam for holographic imaging can be generated.

2. An apparatus as in claim 1 including:
  (a) a second linear subarray of transmitting transducer elements co-planar with the first subarray, each element of the subarray being elongate and having a principal axis normal to the first axis; and
  (b) a second removable mechanical shutter adapted to block the elongate transmitting elements in the second subarray during holographic imaging so that a dispersive acoustic beam can be generated by the apparatus.

3. An apparatus as in claim 1 including means for energizing a plurality of the transmitting elements in a predetermined pattern so that the acoustic energy produced by said elements is phase-reinforced to produce a collimated beam of acoustic energy for pulse-echo imaging.

4. An apparatus as in claim 1 including:
  (a) means for positioning the shutter to block a substantial portion of the transmitting elements; and
  (b) means for energizing the transmitting elements to produce a dispersive beam of acoustic energy for holographic imaging.

5. A linear transducer array for both pulse-echo and holographic acoustic imaging, comprising:
  (a) a linear subarray of transmitting transducer elements disposed in a plane and along a first axis, each element of the subarray being elongate and having a principal axis normal to the first axis, when pulsed each element transmits acoustic waves that are generally collimated in the plane of the principal axis and generally dispersive in the plane of the first axis; and
  (b) a linear subarray of receiving transducer elements co-planar with the transmitting subarray and disposed parallel to the first axis, each element in the receiving subarray being sized sufficiently small to detect signal phase information with substantially non-directional sensitivity in order to provide phase coherence for holographic acoustic imaging and to have a wide angle of acceptance to off-axis incident waves in pulse-echo imaging.

6. An apparatus as in claim 5 including a second linear subarray of transmitting transducer elements co-planar with the first subarray, each element of the subarray being elongate and having a principal axis normal to the first axis, when pulsed each element transmits acoustic waves that are generally collimated in the plane of the principal axis and generally dispersive in the plane of the first axis.

7. An apparatus as in claim 5 in which the transducer elements in the receiving subarray are each dimensioned to be no larger than the length of two times the wave length of the acoustic waves incident on the array so that the receiving subarray has a large angle of acceptance to off-axis incident waves and detects signal phase information with substantially non-directional sensitivity.

8. Apparatus for receiving acoustic waves, comprising:
  (a) a linear array of receiving elements disposed in a plane and along a first axis;
  (b) a plurality of buffer amplifiers for individually amplifying the signals detected by the receiving elements, each buffer amplifier both receives power and transmits signals through a single conductor;
  (c) a plurality of cascode amplifiers each driven by a buffer amplifier and each providing a large output signal voltage corresponding to the acoustic waves detected by the receiving elements; and (d) switch means connected to the cascode amplifiers for selecting a desired cascode amplifier and corresponding receiving element from among the receiving elements in the linear array.

9. An apparatus as in claim 8 wherein each cascode amplifier serves as both an electronic switch and an amplifier and wherein the switch means actuates a desired cascode amplifier so that the signals detected by the desired receiving element are amplified and transmitted through the conductor for subsequent processing.

10. Apparatus for ultrasonically inspecting mechanical components, comprising:
   (a) a transducer array having both transmitting elements and receiving elements;
   (b) a removable mechanical shutter adapted to block a portion of the transmitting elements for holographic imaging;
   (c) means for energizing the array so that a steerable collimated beam of acoustic waves is propagated for pulse-echo imaging and a dispersive beam of acoustic waves is propagated for holograph imaging; and
   (d) means for mechanically translating the array with respect to a mechanical component so that the mechanical component can be inspected ultrasonically.

11. An apparatus as in claim 10 including means for amplifying and for processing acoustic waves detected by the receiving elements during both pulse-echo and holographic ultrasonic imaging.

12. A method of ultrasonically inspecting mechanical components, comprising the steps of:
   (a) energizing sequentially an array of transmitting transducer elements so that a steerable beam of collimated acoustic waves is propagated therefrom;
   (b) detecting the acoustic waves with an array of receiving transducer elements so that a pulse-echo image of the mechanical components can be obtained;
   (c) energizing a restricted portion of an array of the same transmitting transducer elements so that a dispersive beam of acoustic waves is propagated therefrom; and
   (d) detecting the acoustic waves with an array of receiving transducer elements so that a holographic image of the mechanical components can be obtained.

13. A method as in claim 12 wherein the step of energizing the array so that a dispersive beam of acoustic waves is produced includes the step of blocking a predetermined portion of the transmitting transducer elements with a shutter so that a dispersive acoustic beam is propagated therefrom for holographic imaging.

14. A method as in claim 12 including the steps of:
   (a) electrically scanning the steerable beam of collimated acoustic waves across a mechanical component;
   (b) electrically scanning the dispersive beam of acoustic waves across the mechanical component; and
   (c) physically scanning the arrays of transmitting and receiving elements across the mechanical components.

15. An apparatus for receiving acoustic waves and for processing signals corresponding thereto, comprising:
   (a) a linear array of receiving elements disposed in a plane and along a first axis, each element being adapted for converting the acoustic waves incident thereon into corresponding analog output signals;
   (b) means for digitizing the analog output signals from the receiving elements by detecting and quantitizing the envelope of the output signals;
   (c) shift register means constituting a digital delay line with multiple output taps, said shift register means being adapted for delaying the digitized signals by predetermined time intervals; and
   (d) a digital to analog converter for converting the delayed, digitized signals from the shift register means into corresponding analog signals.

16. An apparatus as in claim 15 including a preamplifier connected between each receiving element and the digitizing means for amplifying the analog output signals from the elements and means for sampling the amplified output signals so that the linear array of receiving elements is scanned in a predetermined manner.

17. An apparatus as in claim 15 in which the shift register means includes:
   (a) a random access memory for storing the digitized signals from receiving elements;
   (b) a latch connected to the random access memory; and
   (c) an address encoder for the random access memory for determining the time interval of signal delay.

18. An apparatus as in claim 15 including:
   (a) a plurality of digital delay line-shift registers adapted for delaying the digitized signals from the receiving elements by predetermined amounts;
   (b) means for connecting the receiver elements to the plurality of delay line-shift registers so that the linear array is scanned in a predetermined manner; and
   (c) a summer for combining the outputs from the delay line-shift registers into a composite output signal.

19. An apparatus for receiving acoustic waves and for processing signals corresponding thereto, comprising:
   (a) a linear array of receiving elements disposed in a plane and along a first axis, each element being adapted for converting the acoustic waves incident thereon into corresponding analog output signals;
   (b) a plurality of analog signal delaying channels, each channel including a distributed constant analog delay line and an analog multiplexer for selecting the time delay interval achieved by the distributed constant delay line; and
   (c) means for connecting the output signals from the receiving elements to the analog delaying channels so that the linear array is scanned in a predetermined manner.

20. An apparatus as in claim 19 including:
   (a) means for commanding each analog multiplexer to select a predetermined time delay interval; and
   (b) means for summing the outputs from the analog delay channels into a composite output signal.

* * * * *